United States Patent
Simmons et al.

(10) Patent No.: US 10,183,876 B2
(45) Date of Patent: *Jan. 22, 2019

(54) ELECTROLYTIC CELL AND SYSTEM FOR TREATING WATER

(71) Applicant: Process Solutions, Inc., Poway, CA (US)

(72) Inventors: Brent A. Simmons, Palo Alto, CA (US); Gunnar T. Thordarson, Los Gatos, CA (US); James C. Robertson, San Jose, CA (US)

(73) Assignee: PSI Water Technologies, Inc., Campbell, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 14/702,406

(22) Filed: May 1, 2015

(65) Prior Publication Data
US 2015/0299008 A1    Oct. 22, 2015

Related U.S. Application Data

(63) Continuation of application No. 13/026,947, filed on Feb. 14, 2011, now Pat. No. 9,039,902, which is a
(Continued)

(51) Int. Cl.
*C02F 1/68* (2006.01)
*B01F 5/02* (2006.01)
(Continued)

(52) U.S. Cl.
CPC .............. *C02F 1/68* (2013.01); *B01F 5/0068* (2013.01); *B01F 5/0206* (2013.01);
(Continued)

(58) Field of Classification Search
CPC ...... C02F 2001/461; C02F 2001/46128; C02F 2001/46185; C02F 2201/461;
(Continued)

(56) References Cited

U.S. PATENT DOCUMENTS 2,049,559 A * 8/1936 Evans .................... C02F 1/686
                                                          137/114
2,126,164 A    8/1938 Anderson
(Continued)

FOREIGN PATENT DOCUMENTS

| JP | 2000167575 A | 6/2000 |
|---|---|---|
| WO | 0000433 A2 | 1/2000 |
| WO | 2004108613 A1 | 12/2004 |

*Primary Examiner* — Joseph W Drodge
(74) *Attorney, Agent, or Firm* — The Webb Law Firm

(57) ABSTRACT

A water treatment system is disclosed having electrolytic cell for liberating hydrogen from a base solution. The base solution may be a solution of brine for generating sodium hypochlorite, or potable water to be oxidized. The cell has first and second opposing electrode endplates held apart from each other by a pair of supports such that the supports enclose opposing sides of the endplates to form a cell chamber. One or more inner electrode plates are spaced apart from each other in the cell chamber in between the first and second electrode plates. The supports are configured to electrically isolate the first and second electrode plates and the inner electrode plates from each other. The first and second electrode plates are configured to receive opposite polarity charges that passively charge the inner electrode plates via conduction from the base solution to form a chemical reaction in the base solution as the base solution passes through the cell chamber.

21 Claims, 12 Drawing Sheets

Related U.S. Application Data continuation of application No. 11/450,968, filed on Jun. 9, 2006, now Pat. No. 7,897,022.

(60) Provisional application No. 60/689,607, filed on Jun. 10, 2005.

(51) Int. Cl.

| | | |
|---|---|---|
| *C02F 1/52* | (2006.01) | |
| *C02F 1/46* | (2006.01) | |
| *B01F 5/00* | (2006.01) | |
| *G01N 1/20* | (2006.01) | |
| *C02F 1/467* | (2006.01) | |
| *C25B 1/26* | (2006.01) | |
| *C25B 9/06* | (2006.01) | |
| *C25B 9/20* | (2006.01) | |
| *C02F 1/00* | (2006.01) | |
| *C02F 1/469* | (2006.01) | |
| *C02F 1/461* | (2006.01) | |

(52) U.S. Cl.
CPC .......... *C02F 1/4672* (2013.01); *C02F 1/4674* (2013.01); *C02F 1/685* (2013.01); *C02F 1/686* (2013.01); *C25B 1/26* (2013.01); *C25B 9/063* (2013.01); *C25B 9/203* (2013.01); *G01N 1/2035* (2013.01); *B01F 2005/0002* (2013.01); *B01F 2005/004* (2013.01); *C02F 1/001* (2013.01); *C02F 1/4696* (2013.01); *C02F 1/5227* (2013.01); *C02F 1/5236* (2013.01); *C02F 2001/46128* (2013.01); *C02F 2001/46142* (2013.01); *C02F 2201/461* (2013.01); *C02F 2201/4611* (2013.01); *C02F 2201/4618* (2013.01); *C02F 2201/46125* (2013.01); *C02F 2201/46145* (2013.01); *C02F 2201/46185* (2013.01); *C02F 2209/005* (2013.01); *C02F 2209/29* (2013.01); *Y02E 60/366* (2013.01); *Y02W 10/37* (2015.05)

(58) Field of Classification Search
CPC .... C02F 2201/46125; C02F 2201/4611; C02F 2201/46145; C02F 2201/46185; C02F 2209/005; C02F 2209/29; C02F 1/008; C02F 2209/003; C02F 2209/14; Y02W 10/37; B01F 5/0206; B01F 5/0068; B01F 2005/0002; B01F 2005/004; B01F 5/0057; B01F 5/02; B01F 5/0218; B01F 5/0231; B01F 5/0256; B01F 5/04; B01F 5/12; B01F 7/02; B01F 13/10; Y02E 60/366; G01N 1/10; G01N 1/20; G01N 1/2035
USPC ......... 73/61.59, 863.01, 864.34; 210/170.05, 210/194, 198.1, 199, 205, 258, 220, 85, 210/96.1; 366/150.1, 160.1, 160.2, 162.4, 366/167.1, 173.1, 173.2, 182.1, 182.2
See application file for complete search history.

(56) References Cited

U.S. PATENT DOCUMENTS

| | | | |
|---|---|---|---|
| 2,307,509 | A | 1/1943 | Joachim et al. |
| 2,353,358 | A | 7/1944 | Prager |
| 2,751,335 | A | 6/1956 | Carver et al. |
| 3,059,243 | A | 10/1962 | Ross et al. |
| 3,326,747 | A | 6/1967 | Ryan et al. |
| 3,361,663 | A | 1/1968 | Murray et al. |
| 3,460,678 | A | 8/1969 | Condolios |
| 3,847,375 | A | 11/1974 | Kuerten et al. |
| 3,897,798 | A | 8/1975 | De Vale |
| 4,059,522 | A | 11/1977 | Polley et al. |
| 4,118,307 | A | 10/1978 | LaBarre |
| 4,306,581 | A | 12/1981 | Alandt |
| 4,313,827 | A | 2/1982 | Ratigan et al. |
| 4,372,851 | A | 2/1983 | Mandt |
| 4,495,048 | A | 1/1985 | Murakami et al. |
| 4,512,887 | A | 4/1985 | Ritke et al. |
| 4,618,426 | A * | 10/1986 | Mandt ................. B01F 7/00741 210/220 |
| 4,997,574 | A | 3/1991 | Sarunac |
| 5,037,518 | A | 8/1991 | Young et al. |
| 5,186,794 | A | 2/1993 | Parker et al. |
| 5,894,995 | A | 4/1999 | Mazzei |
| 5,979,478 | A | 11/1999 | Screptock et al. |
| 6,132,590 | A | 10/2000 | Moran et al. |
| 6,213,134 | B1 * | 4/2001 | Pike ....................... B08B 9/093 134/166 R |
| 6,227,694 | B1 | 5/2001 | Mitake et al. |
| 6,238,557 | B1 * | 5/2001 | Ziemer ................. B01F 3/0865 210/198.1 |
| 6,245,224 | B1 | 6/2001 | Enoki et al. |
| 6,309,523 | B1 | 10/2001 | Prasnikar et al. |
| 6,309,532 | B1 | 10/2001 | Tran et al. |
| 6,375,825 | B1 | 4/2002 | Mauldin et al. |
| 6,746,580 | B2 | 6/2004 | Andrews et al. |
| 6,811,710 | B2 | 11/2004 | Simmons |
| 6,818,124 | B1 | 11/2004 | Simmons |
| 7,001,525 | B2 | 2/2006 | Binot et al. |
| 7,244,348 | B2 | 7/2007 | Fernandez et al. |
| 7,517,460 | B2 | 4/2009 | Tormaschy et al. |
| 9,039,902 | B2 * | 5/2015 | Simmons .............. C02F 1/4672 210/739 |
| 2001/0004962 | A1 | 6/2001 | Hirota et al. |
| 2001/0010296 | A1 | 8/2001 | Hirota et al. |
| 2002/0036134 | A1 | 3/2002 | Shirota et al. |
| 2002/0162802 | A1 * | 11/2002 | Simmons ................ C02F 1/686 210/739 |
| 2003/0039729 | A1 | 2/2003 | Murphy et al. |
| 2005/0058886 | A1 | 3/2005 | Andrews et al. |
| 2005/0145550 | A1 | 7/2005 | Loyd et al. |

* cited by examiner

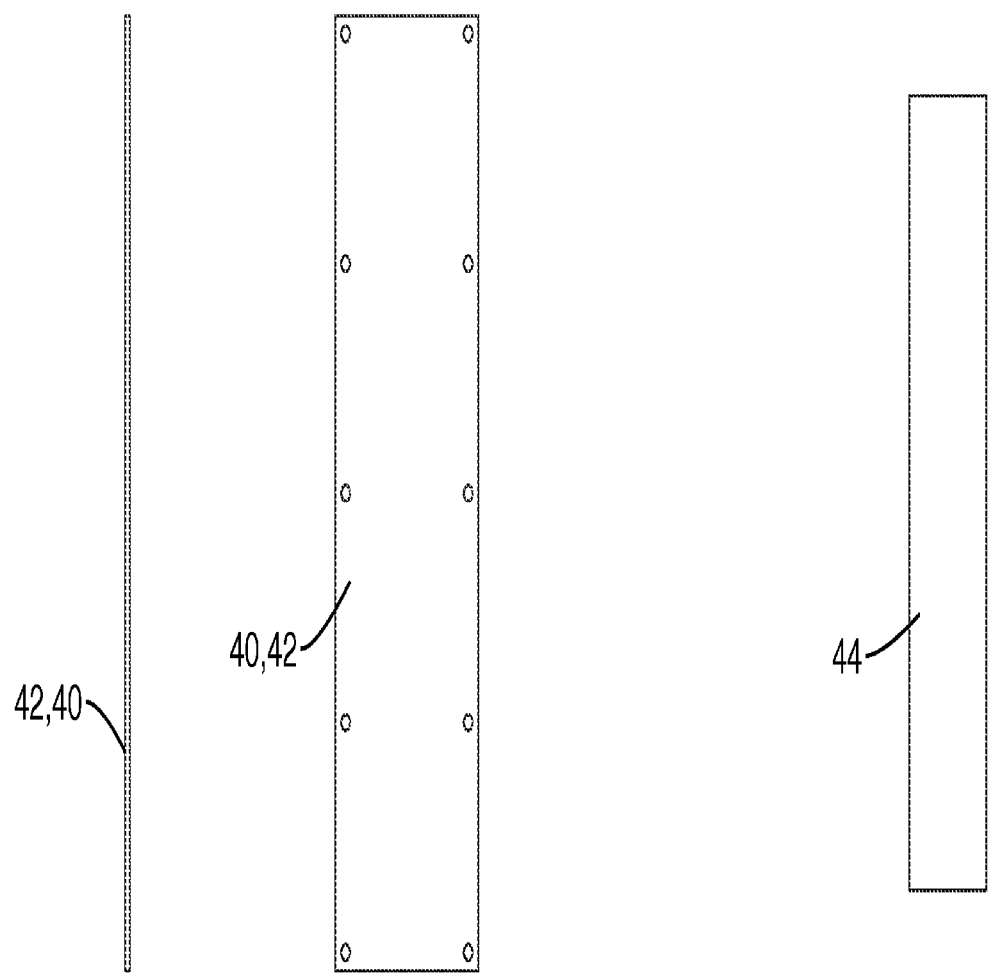

ELECTROLYTIC CELL AND SYSTEM FOR TREATING WATER

CROSS-REFERENCE TO RELATED APPLICATIONS

This application is a continuation of U.S. patent application Ser. No. 13/026,947 filed on Feb. 14, 2011, which is a continuation of U.S. patent application Ser. No. 11/450,968, filed on Jun. 9, 2006, now issued U.S. Pat. No. 7,897,022, which claims priority from U.S. provisional application No. 60/689,607, filed on Jun. 10, 2005, all of which are incorporated herein by reference in their entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to water treatment systems, and more particularly to water treatment systems having electrolytic cells.

2. Description of Related Art

Chlorine is the most common disinfectant used in water and wastewater treatment systems in the world. Among a number of other applications, chlorine is commonly used in applications ranging from potable water, odor and corrosion control, and wastewater treatment to irrigation systems and food and beverage processing.

Historically, gaseous chlorine was the most prevalent form of chlorination system in the United States; however, the use of liquid sodium hypochlorite is increasing in water and wastewater treatment applications due to safety concerns associated with the use, storage and transportation of chlorine gas.

Transporting bulk chlorine on crowded highways and into residential areas has become a major safety concern. Federal and local authorities have recognized this problem and are dictating better solutions to this problem. For example, implementation of the Clean Air Act (CAA) Risk Management Plan (RMP) by the USEPA for the storage of hazardous chemicals (June 1999) and the re-registration of chlorine gas by the USEPA Office of Pesticide Programs as a pesticide (Fall 2001) have further accelerated the use of liquid sodium hypochlorite in the water and wastewater treatment industry.

More stringent regulation of toxic gases and accidental releases of chlorine have required industry professionals to seek alternative methods of disinfection. Pressurized chlorine gas has become regulated to the point where many utilities have evaluated the alternatives and found on-site generation of sodium hypochlorite to be their best available technology for disinfection.

On-site chlorine generation systems have been developed to solve this problem. However, existing systems are inefficient, requiring large amounts of energy to produce the amounts of chlorine required. In addition, existing chlorine generation systems require constant monitoring and frequent maintenance from material buildup in the system.

In addition, most conventional electrochemical processes having D.C. electrodes rely on automatic current control where amperage is fixed and voltage is allowed to float. These systems typically utilize phase angle-fired SCR control of the rectification process, which account for the vast majority, if not all, of the failures related to the D.C. rectification process.

The water storage systems currently used to hold treated water also have drawbacks. These large water reservoirs are prone to water quality problems as they are typically stagnant with as little as one to two percent turnover per day. This lack of turnover allows for biological re-growth, nitrification, and temperature stratification. These factors can all compound to produce a poor or even unhealthy water quality leading to consumer complaints and related water quality issues within the distribution system.

Therefore, an object of the present invention is to provide an improved chlorine generation system that efficiently and reliably generates chlorine from a base solution.

Another object of the present invention is a chlorine generation system that is self-cleaning and therefore requires minimal maintenance to operate.

Yet another object of the present invention is an oxygen generation system that generates oxygen via electrolytic liberation of hydrogen in water.

Yet another object of the present invention is to provide an improved water treatment delivery system.

At least some of the above-mentioned objectives will be met in the invention described hereafter.

BRIEF SUMMARY OF THE INVENTION

An aspect of the invention is an apparatus for liberating hydrogen from a base solution. The apparatus has a cell chamber configured to receive the base solution. The cell chamber is generally bounded by a first electrode on one end, and a second electrode on a second end opposing the first electrode. The first and second electrodes are spaced apart from each other substantially along the length of the cell chamber and electrically isolated from each other. There are one or more inner electrode plates disposed in the cell chamber in between the first and second electrodes that are spaced apart and electrically isolated from each other and the first and second electrodes to form individual cell compartments along the length of the cell chamber. The individual cell compartments are configured to allow the base solution to pass through the cell compartments along the length of the cell chamber. Furthermore, the first and second electrodes are configured to receive opposite polarity charges to form an electrolytic chemical reaction in the base solution as the base solution passes through the cell chamber.

Preferably, the first and second electrodes function as an anode and cathode respectively, such that the current passes from the first electrode, across the base solution and the one or more inner electrode plates, and out to the second electrode.

In one embodiment, the first electrode comprises a first electrode plate, and the second electrode comprises a second electrode plate, such that the first and second electrode endplates forming outer walls of the cell chamber.

The apparatus may further comprise a pair of supports holding the first and second electrode endplates spaced apart from each other, the supports enclosing opposing sides of the endplates to form a cell chamber, and electrically insulating the first and second electrode plates and the inner electrode plates from each other.

Generally, the inner electrode plates are passively charged via conduction of the base solution such that they function as bipolar electrodes. The electrode plates may be configured to liberate hydrogen from a base solution of salt and water, resulting in generation of sodium hypochlorite. The plates may also be configured to liberate hydrogen from a base solution of water to generate oxygen to oxidize the water. The electrode plates are coated with varying catalytic materials such as DSA or platinum to facilitate the reaction for different base solutions.

Another aspect is a method for liberating hydrogen from a base solution. The method includes the steps of directing the base solution through a cell chamber defined by first and second electrodes wherein the first and second electrodes are electrically isolated when in the absence of the base solution, and applying a current across the first and second electrodes. One or more internal electrodes are passively charged via conduction from the base solution to form an electrolytic chemical reaction in the base solution to liberate hydrogen from the base solution.

Yet another aspect of the present invention is an electrolytic cell for liberating hydrogen from a base solution. The cell has a first and second opposing electrode endplates, a support structure holding the first and second electrode endplates spaced apart from each other and enclosing opposing sides of the endplates to form a cell chamber. One or more inner electrode plates spaced apart from each other in the cell chamber in between the first and second electrode plates. The inner electrode plates are aligned with the first and second electrode plates in an orientation substantially parallel to a flow direction of the base solution. Furthermore, the first and second electrode plates are configured to receive an electrical current to form an electrolytic chemical reaction in the base solution as the base solution passes through the cell chamber.

In a further aspect, a method is disclosed for generating sodium hypochlorite from a base solution of water and salt. The method comprises directing the base solution through an electrolytic cell having opposing electrode endplates, supplying current to the endplates such that each of the endplates has a charge of opposite polarity from each other, passively charging one or more inner electrode plates positioned between the opposing electrode endplates, and liberating hydrogen from the base solution to form sodium hypochlorite. The one or more inner electrode plates may have direct contact with the base solution such that each inner electrode plate forms a bipolar electrode In one embodiment of the current aspect, the method further comprises automatically separating the hydrogen from the sodium hypochlorite to separate output lines via density differentials between the hydrogen and the sodium hypochlorite.

In a second embodiment, the method further includes controlling the current across the electrolytic cell by modifying the content of the base solution.

Yet another aspect is a system for liberating hydrogen from a base solution. The system includes an electrolytic cell having an input for receiving the base solution to generate a modified solution by liberating hydrogen from the base solution. The electrolytic cell has an output with a bifurcated line configured such that the modified solution is passively directed out a first line while the liberated hydrogen is passively directed out a second line to remove the liberated hydrogen from the modified solution.

Preferably, first line is coupled to the input to circulate at least a portion of the modified solution back into the electrolytic cell.

The system is configured to be modular so that one or more additional electrolytic cells may be connected in fluid communication with the first electrolytic cell. For example the first line is further bifurcated to direct at least a portion of the modified solution through a third line leading to second electrolytic cell. Correspondingly, the first line leading from the output of the second cell then directs the modified solution to the input of the third cell. This process is completed until all of modified solution is passed though all of the cells.

Ideally, the modified solution leading into the second electrolytic cell is substantially free of liberated hydrogen.

Generally, a density differential between the modified solution and the liberated hydrogen passively drives the liberated hydrogen out the second line. Each of the lines may have different diameters to create a differential in pressure across the different lines.

In one embodiment of the current aspect, a rectifier is coupled to the first electrolytic cell. The rectifier is configured to supply a constant current to the first electrolytic cell such that the current across the first electrolytic cell is controlled via the content of the base solution passing through the first electrolytic cell.

For a brine solution the electrolytic cell is configured to generate sodium hypochlorite from the brine solution. A brine supply may be coupled to the input of the first electrolytic cell, with a pump configured to feed the base solution into the first electrolytic cell. The pump is ideally configured to incrementally adjust the flow rate of brine in the base solution to control the current across the electrolytic cell.

Preferably, the electrolytic cell is oriented vertically, such that the base solution travels upward through the electrolytic cell against gravity.

Yet another aspect is a method for liberating hydrogen from a base solution. The method includes the steps of directing the base solution through an electrolytic cell, supplying a current to the electrolytic cell to separate hydrogen from the base solution to create a mixture of liberated hydrogen and a modified solution, directing the liberated hydrogen and modified solution through a junction having a first line and a second line, and passively separating the liberated hydrogen from the modified solution by directing the modified solution into the first line and the liberated hydrogen into the second line.

A further aspect is an apparatus for liberating hydrogen from a base solution, comprising an electrolytic cell having a chamber configured to receive the base solution, and a rectifier coupled to the first electrolytic cell. The rectifier is configured to supply a constant voltage to the first electrolytic cell to liberate hydrogen from the base solution. The apparatus further includes a pump configured to meter the electrolytic content of the base solution such that the effective current across the electrolytic cell is indirectly controlled via the electrolytic content, and therefore the conductivity, of the base solution passing through the first electrolytic cell.

The pump is preferably configured to incrementally adjust the concentration of the electrolytic content in the base solution. In one embodiment, the pump comprises a magnetically driven gear pump.

In another embodiment, the electrolytic cell comprises a chamber defined by a pair of opposing electrodes that are spaced apart such that they are separated by and in intimate contact with said base solution, so that the effective current across the opposing electrodes is controlled by varying the conductivity of the base solution in the cell chamber.

For a brine based solution comprising salt and water, the electrolytic cell is configured to generate sodium hypochlorite and hydrogen from the base solution, and the pump is configured to incrementally adjust the concentration of the brine in the base solution to control the current across the electrolytic cell.

In another embodiment, the rectifier comprises a fully isolated step-down transformer and bridge rectifier. A programmable logic controller may also be coupled to the pump to adjust the output of the pump in real time to control the effective current across the electrolytic cell.

Yet a further aspect is a method for liberating hydrogen from a base solution, comprising directing the base solution through an electrolytic cell, supplying a constant current to the electrolytic cell to separate hydrogen from the base solution, and adjusting the content of the base solution to control an effective current across the electrolytic cell. Preferably, the current across the electrolytic cell is controlled without SCR, phase angle, or wave form modification.

Another aspect is treatment delivery system for treatment of a body of water held in a reservoir. The system includes a first line configured to deliver a jet of water into the body of water at a location in the reservoir, and a second line configured to deliver a treatment solution into the body of water at the location. The second line has an opening at its end to release the treatment solution at the location. The second line is coupled to a pump, located external to the reservoir, for directing the treatment solution into the reservoir. In addition, the first line is oriented with respect to the second line such that the jet of water diffuses the treatment solution into the body of water.

In one embodiment of the current aspect, the jet of water is oriented at a path generally perpendicular to the release of the treatment solution.

The first line comprises a nozzle at its end to generate the jet of water at the location. The nozzle is preferably located at a lower region in the reservoir, and oriented to expel the jet of water upward into the tank across a generally horizontal release of the treatment solution. The motive force for the jet of water is provided by the head pressure in the water injection line.

In one embodiment, the system includes an analyzer coupled to a sampling line leading into the reservoir. The analyzer is configured to measure the quality of the water and is coupled to the pump such that the flow rate of the treatment solution provided by the pump may be adjusted according to measurements from the analyzer.

Yet another aspect is a method for treating a body of water held in a reservoir. The method includes the steps of generating a jet of water into the body of water at a location in the reservoir, and separately delivering a treatment solution into the body of water to the location. The treatment solution is released into the body of water at the location such that the jet of water is directed at the release to diffuse the treatment solution into the body of water.

A further aspect is a method of decontaminating a supply of water, comprising the steps of directing the water through an electrolytic cell to oxygenate the water, directing the water through an electro-phoretic cell to infuse the water with iron ions, wherein the iron ions are configured to flocculate with contaminant particles, and filtering the flocculated contaminant particles from the water.

In one embodiment of the current aspect, the flocculated contaminant particles are filtered with a diatomaceous earth filter. The flocculated water may also be processed with a pre-coat prior to being filtered.

Yet a further aspect is system for decontaminating a supply of water, including an electrolytic cell configured to receive the water to oxygenate the water, an electro-phoretic cell coupled to the output of the electrolytic cell, wherein the electro-phoretic cell is configured to infuse the water with iron ions to flocculate contaminant particles in the water, and a filter configured to separate the flocculated contaminant particles from the water.

A further aspect is a method of oxidizing water, comprising directing water through an electrolytic cell having opposing electrode endplates, supplying current to the endplates such that each of the endplates has a charge of opposite polarity from each other, passively charging one or more inner electrode plates positioned between the opposing electrode endplate, and liberating hydrogen from the water to generate oxygen.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 9 illustrates an electrode endplates in accordance with the present invention.

FIG. 10 illustrates an inner electrode plate in accordance with the present invention.

DETAILED DESCRIPTION OF THE INVENTION

Referring more specifically to the drawings, for illustrative purposes the present invention is embodied in the apparatus generally shown in FIG. 1 through FIG. 13. It will be appreciated that the apparatus may vary as to configuration and as to details of the parts, and that the method may vary as to the specific steps and sequence, without departing from the basic concepts as disclosed herein.

1. Sodium Hypochlorite Generation and Storage

Figure 1:
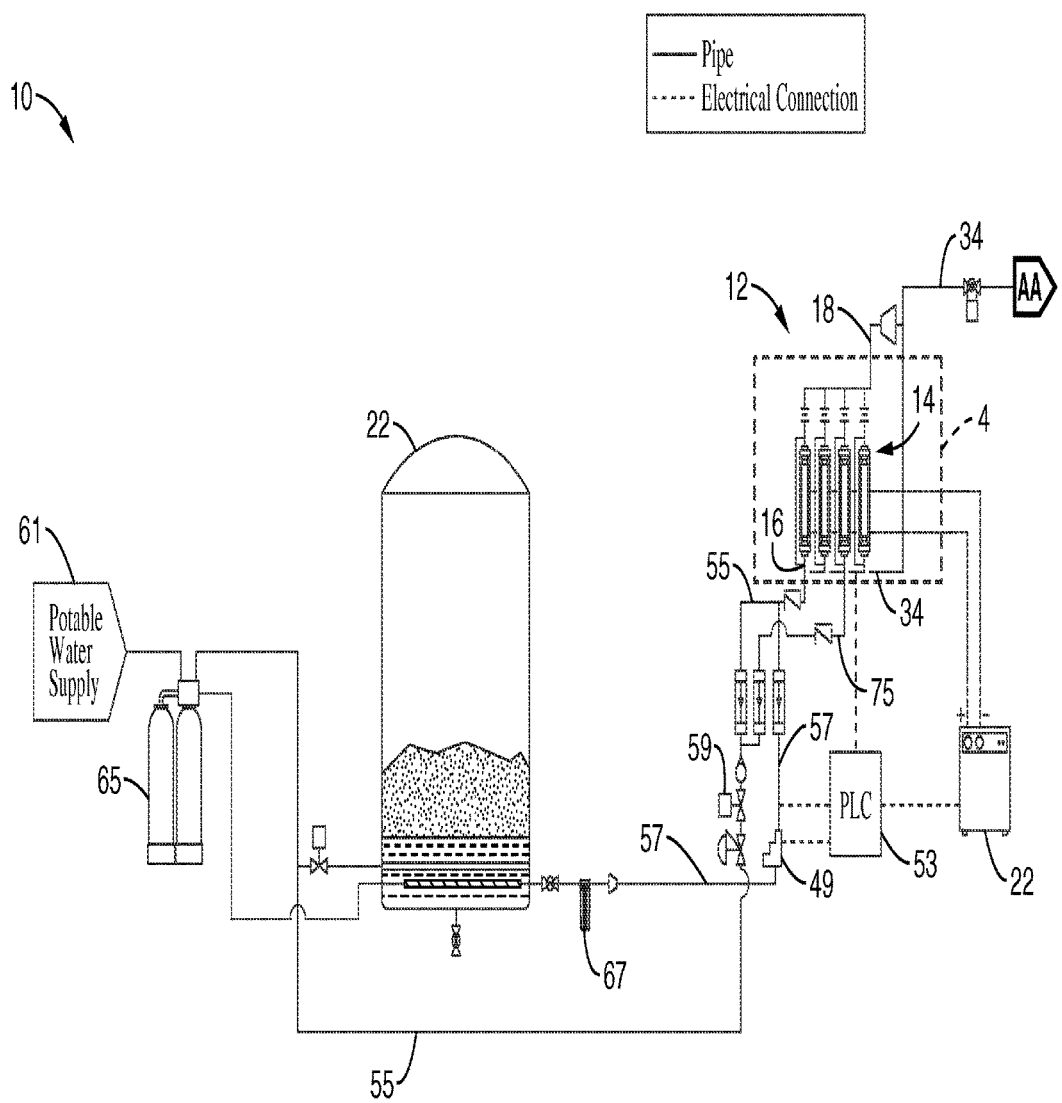
FIG. 1 is a schematic view of a system for generating hypochlorite from a solution of brine in accordance with the present invention.

Referring to FIG. 1, an on-site sodium hypochlorite system 10 is disclosed. The sodium hypochlorite system 10 is configured to produce a weak bleach solution from a base solution of ordinary salt, water and electrical power. The process typically outputs a sodium hypochlorite solution, e.g. "bleach," having a concentration in the range of 0.8-1.0% available chlorine. As a reference, household bleach such as Clorox is typically 5-6%, while liquid pool chlorine is 12-13%.

Solar grade salt is first dissolved with water a potable water supply 61 to form a concentrated brine solution. The water may be processed with water softener 65 prior to treatment. A source tank 20 may be used to store the brine or base solution such that the brine may be readily (and continuously) fed into electrolytic cell array 12. A brine-maker or similar device may also be included or integrated with the source tank 20.

Pump 49 feeds the brine solution (which may be filtered with filter 67) along line 57. The brine solution is then diluted with water from line 55 fed into inlet 16 of the electrolytic cell array 12.

The primary processing of the base solution (e.g. brine) is performed by a rack or array 12 of electrolytic cells 14. The array 12 comprises a plurality of electrolytic cells 14 (four shown in FIG. 1) connected in series in fluid communication with each other. It will be appreciated that any number of electrolytic cells 14 may be used to vary the output of the system 10. The system 10 as specified in FIG. 1, is configured to generate 80 lbs. (approximately 20 lbs. per cell) of sodium hypochlorite a day. However this output may be varied by typical design modifications commonly used in the art.

The electrolytic process, explained in further detail below, converts the brine solution to sodium hypochlorite and hydrogen ($H_2$), which are output into line 34.

Figure 2:
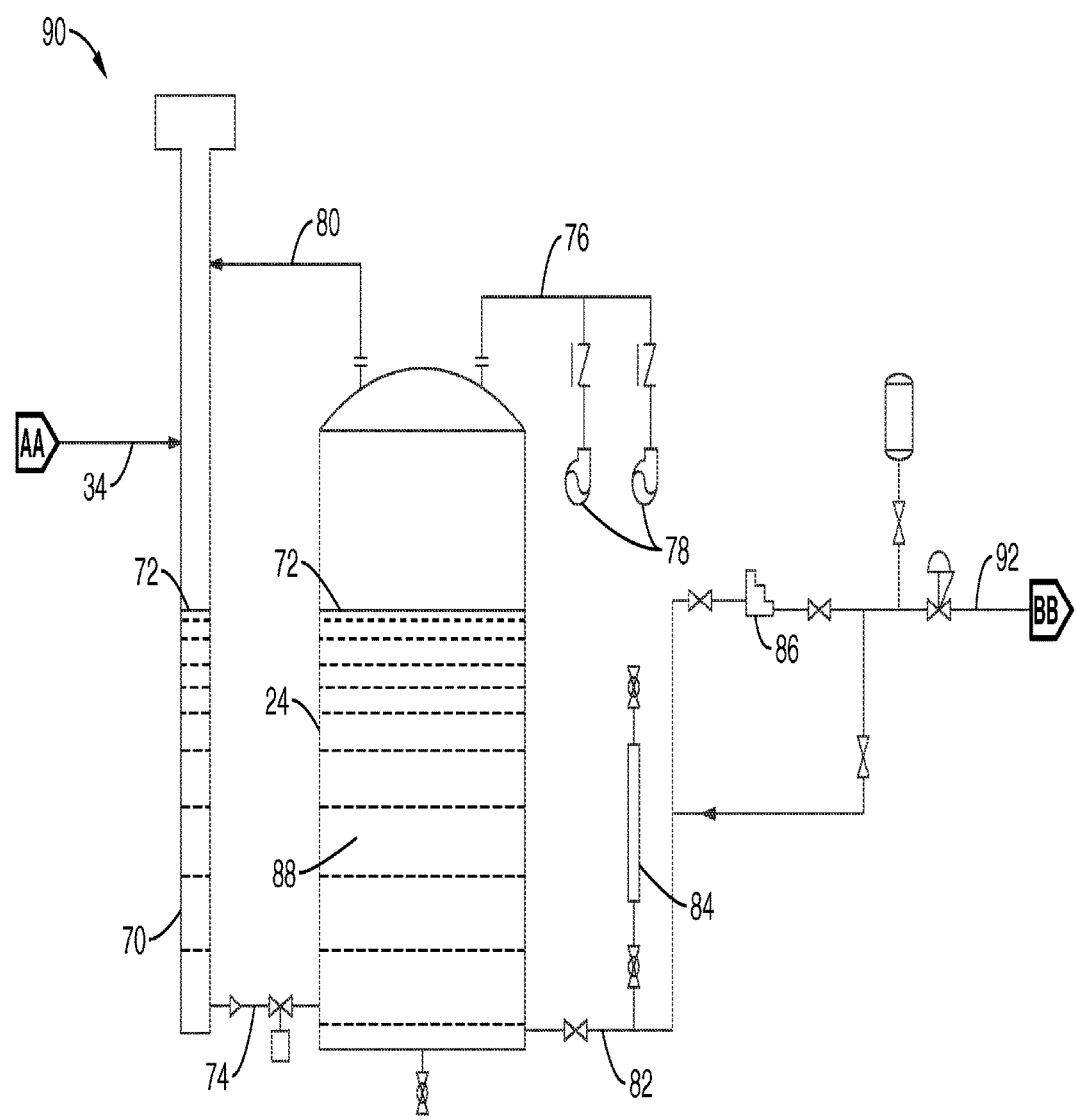
FIG. 2 illustrates an exemplary hypochlorite storage system in accordance with the present invention.

Referring now to FIG. 2, the hypochlorite is fed via line 34 into sodium hypochlorite storage tank 24 designed to accommodate one or more day's supply. The evolved hydrogen also present in line 34 is not directed to the storage vessel 24, but rather to active standpipe 70. The sodium hypochlorite 88 is directed from the bottom of the standpipe to the storage vessel 24 via line 74. Hydrogen dilution blowers 78 are directed into the top of storage vessel 24 via line 76, thus directing any secondary dilution air from the storage vessel head space to standpipe 70 via line 80. The blowers are preferably configured to release the hydrogen into the atmosphere to the dilute hydrogen in the tank to below 25% LEL or 1% of hydrogen by volume, thus precluding the presence of an explosive environment.

When the system registers that the level 72 of hypochlorite 88 in the tank 24 is getting low, the generation system 10 automatically restarts to replenish the supply.

Figure 3:
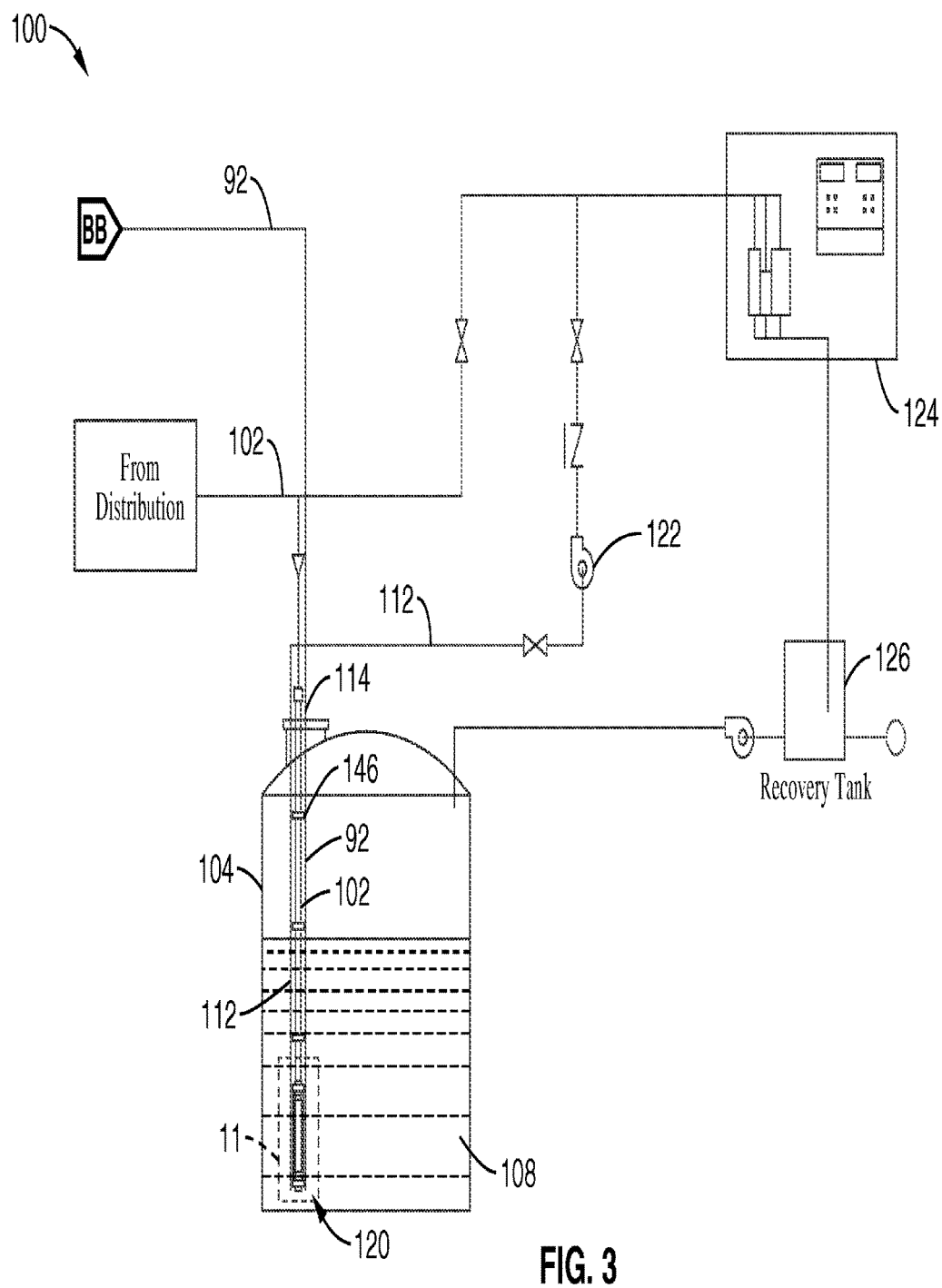
FIG. 3 illustrates an exemplary treatment delivery system in accordance with the present invention

On or more metering pumps 86 then transfers the sodium hypochlorite solution 88 from the storage tank 24 via line 82 to one or more dosing points for treatment, as shown in FIG. 3 (described in further detail below).

Figure 4:
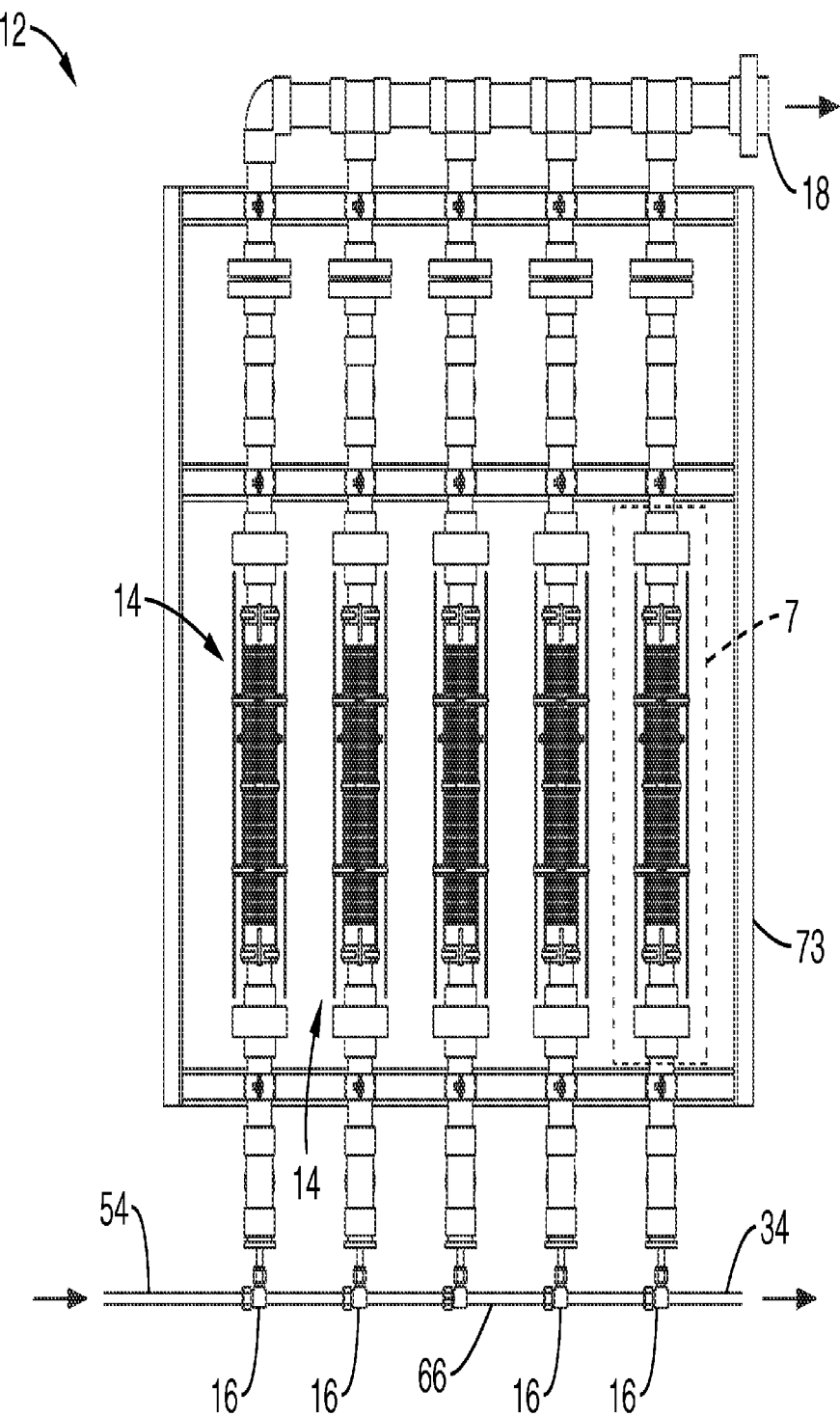
FIG. 4 illustrates an electrolytic cell array in accordance with the present invention.
Figure 5:
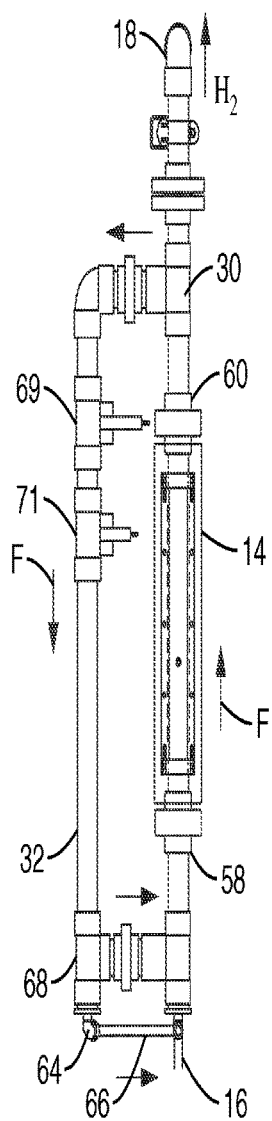
FIG. 5 shows a side view of the electrolytic cell array of FIG. 4.
Figure 6:
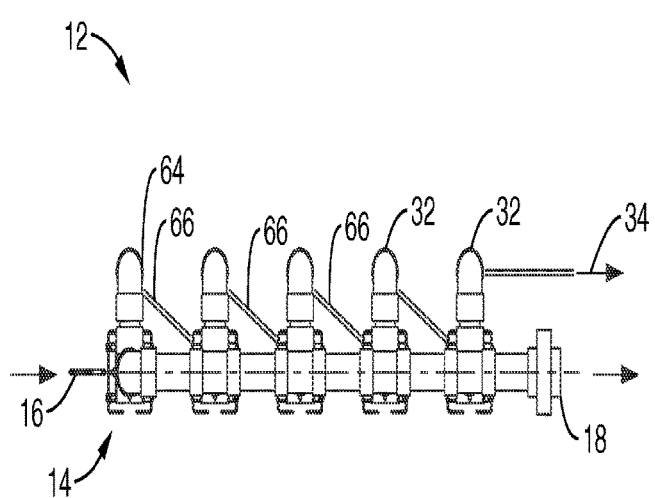
FIG. 6 shows a top view of the electrolytic cell array of FIG. 4.

FIGS. 4-6 further illustrate the electrolytic cell array 12 for sodium hypochlorite generation. The array 12 functions passively to allow all produced hydrogen to be removed from each cell compartment 14 by the density differential created during the electrolytic process. Thus, no hydrogen generated in a first cell or compartment will be delivered to the next compartment. This vastly improves existing technologies that force the produced hydrogen from one cell compartment to the next, such that a blockage in any one compartment can have catastrophic results.

As shown in FIG. 4, array 12 comprises five electrolytic cells 14 that are vertically plumbed hydraulically in series. Frame 73 may also be implemented to retain the cells. The array 12 is configured to be modular, such that a minimum of one cell 14 may be used for lower duty applications, and additional cells may be readily added to increase output. The diluted brine solution is fed into input 16 of the first cell from source tank 20. The solution then passes through the first electrolytic cell 14 (described in more detail below), while current is being applied to process the base solution. The conversion process liberates hydrogen from the brine solution according to the following chemical reaction:

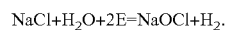

$$NaCl+H_2O+2E=NaOCl+H_2.$$

Referring to FIG. 5, the sodium hypochlorite (NaOCl) and hydrogen ($H_2$) are both fed out of the first cell outlet 60 and toward junction 30. The junction 30 is configured such that the density differentials between the sodium hypochlorite and the hydrogen passively separate into different dedicated bifurcated lines. The modified solution (containing a small percentage of sodium hypochlorite) is directed down return line 32 (which may comprise 1.5 in. PVC tubing), while the hydrogen vents vertically out a second line to output 18. The entrained hydrogen in the cell leg as compared to the return leg 32 results in as much as a 10% differential corresponding to a positive upward flow.

As shown in FIGS. 5 and 6, the return line 32 then reaches a second junction 68, wherein a portion of the modified solution is cycled back through the cell 14, and another portion of the modified solution is directed through smaller feed tube 66 (e.g. ¾ in. tubing) to the input 16 of the second cell of the series. The process is repeated until the solution has passed through all the cells and into line 34. The entrained hydrogen is vented out through line 18, which then feeds back into line 34.

The return line 32 of each cell may also have a level sensor 69 and temperature switch 71 to preclude exposing an active electrode surface.

Figure 7:
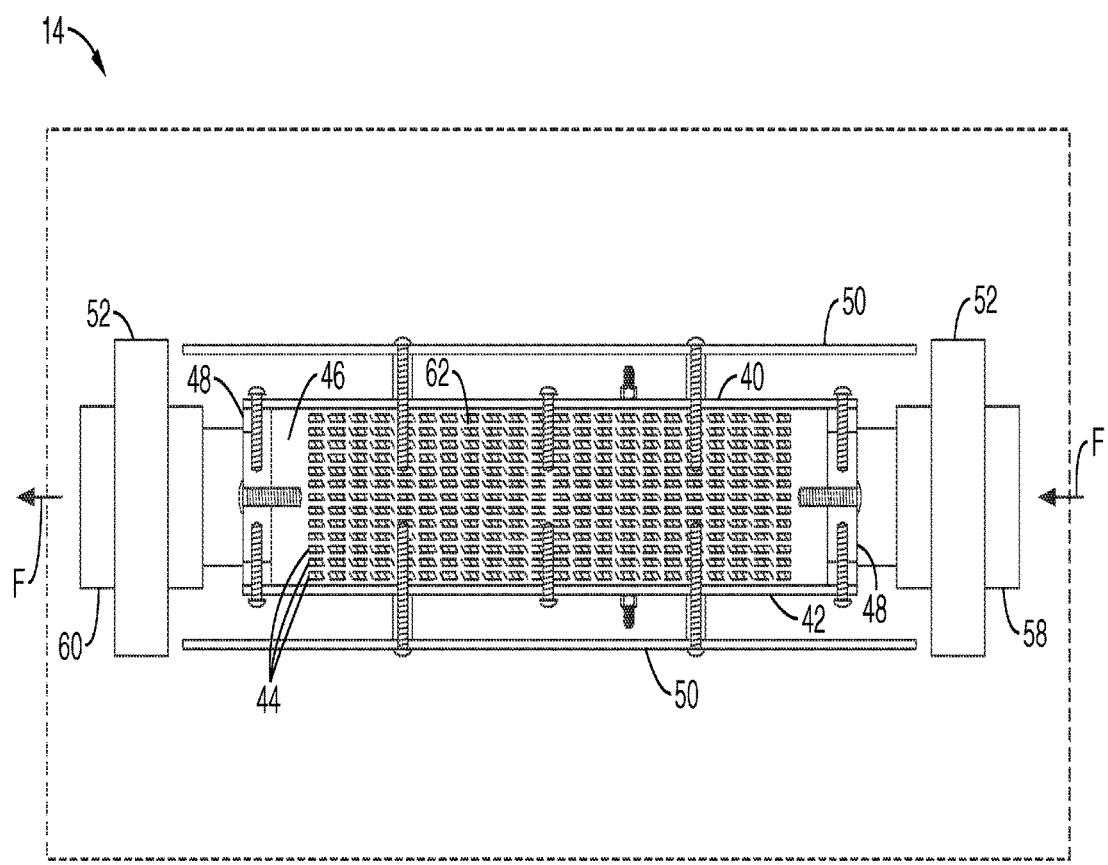
FIG. 7 illustrates a side view electrolytic cell having floating bipolar electrodes in accordance with the present invention.
Figure 8:
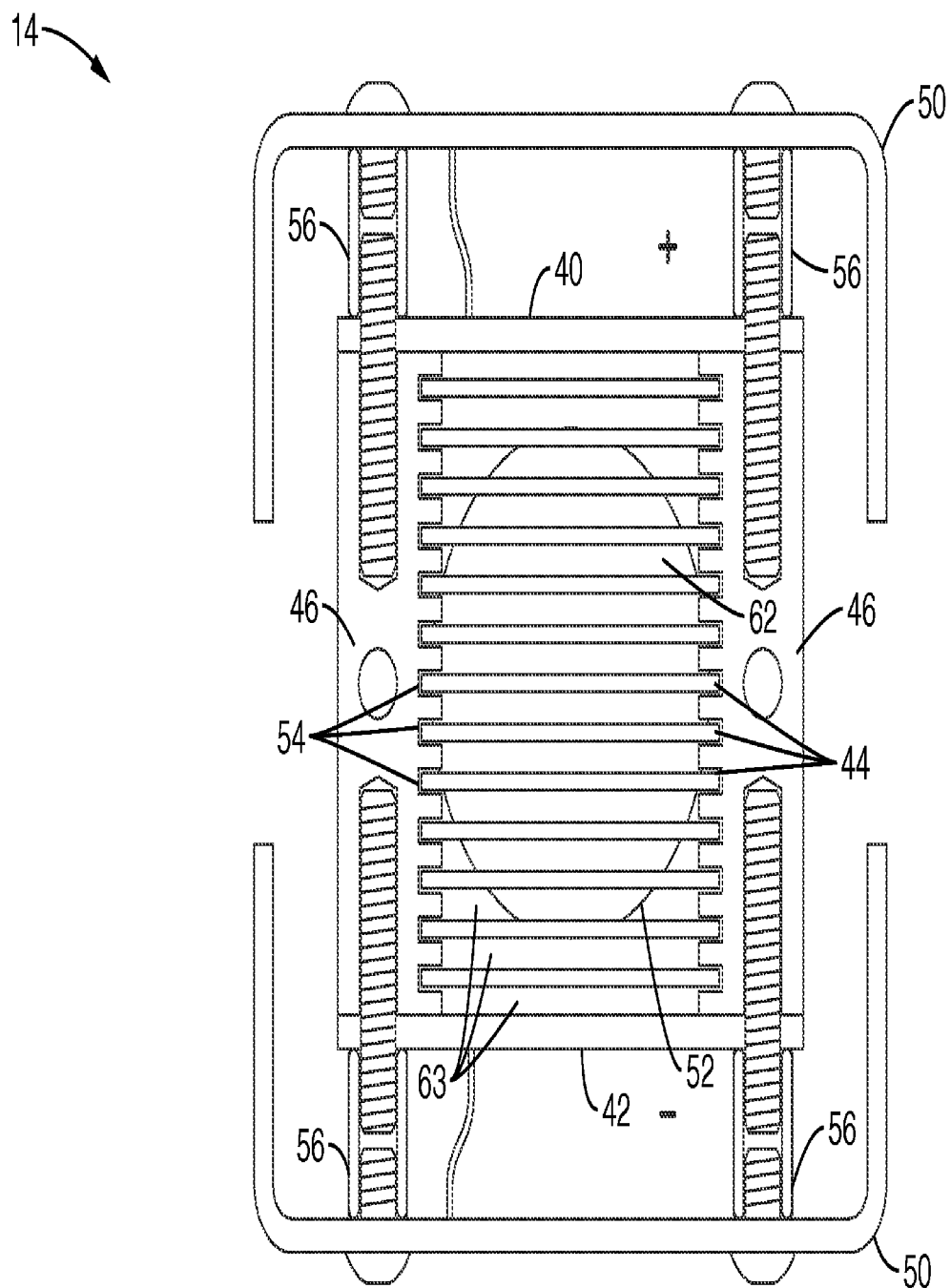
FIG. 8 illustrates an expanded end view of the electrolytic cell of FIG. 7.

FIGS. 7 and 8 further illustrate the structure of the electrolytic cell 14. The cell has a first electrode comprising an upper electrolytic endplate 40 and second electrode comprising a lower electrolytic endplate 42, both of which are supported at a spaced distance from each other via a pair of plate guides or support 46. The supports 46 and endplates 40, 42 form a chamber 62 in between inlet 58 and outlet 60 of couplings 52 through which the base solution is guided. The supports 46 also have a series of grooves 54 that allow positioning of a series of inner electrode plates 44 that are suspended in the chamber 62. The inner electrode plates 44 and endplates 40 and 42 are substantially aligned parallel to each other with planar surfaces substantially in line with the flow direction F. The inner electrode plates 44 are spaced apart from each other and the endplates such that they form a plurality of individual compartments 63 through which the base solution passes.

Supports 46 are preferably made of acrylic or similar material that is electrically insulating such that electrical current does not flow between any of the inner plates and endplates in the absence of a current-carrying solution. Furthermore, the acrylic may be transparent to provide direct visual inspection of the internal chamber 62 and plate surfaces. End caps 48, which may also comprise acrylic or similar material, abut against supports 46 to close off chamber 62. No elastomer gasketing or internal baffles are necessary.

A pair of electrode shields 50 may also be positioned around the endplates via standoffs 56. The shields 50 protect from inadvertent contact with the charged electrodes, and are preferably transparent to allow for visualization of the cell.

As shown in FIG. 8, current is applied at the endplates 40, 42 such that each act as a positive and negative terminal for the applied voltage needed for the conversion process. In other words, plate 40 acts as an anode, and plate 42 a cathode with the current passing between the anode 40 to cathode 42. With the solution passing through the cell chamber 62, the inner electrolyte plates 44 are essentially "floating" electrically in series within the chamber. The current flows from the first endplate 40, across each individual compartment 63 via conduction from the electrolytic solution, to each of the electrolyte plates 44, i.e. the electrolyte plates 44 do not have direct electrical leads applied to them, but are "passively charged." Thus, the opposing surfaces of each of the electrolyte plates have an opposite charge, forming a bipolar electrode. The current flows through each of the electrolytic plates until reaching the second endplate or cathode 42, completing the electric circuit.

The mono-polar outer electrode plates 40/42 ensure that there are no wetted DC terminals. With the configuration as shown in FIGS. 7 and 8, the bipolar electrodes result in 14 active cell surfaces within each cell.

FIGS. 9 and 10 illustrate electrode endplates 40/42, and electrode 44, both of which are preferably comprised of titanium. Both surfaces of the inner electrolytic plates 44 and the inner surface of the electrolytic endplates 40, 42 are plated with a catalytic coating to facilitate the desired conversion process. For example, for generation of sodium hypochlorite, the plates are preferably coated with a mixed metal oxide catalytic coating, e.g. DSA® from ELTECH Systems Corp. The endplates and electrode surface areas may also be varied to generate larger sodium hypochlorite volumes. For example, production may be varied by using 2 in.×12 in., 4 in.×12 in., or 6 in.×12 in. or greater plates.

Referring back to FIG. 1, general operation of the generation system 10 is effected by controller 53: Controller 53 is preferably a PLC (Programmable Logic Controller), such as an Allen Bradley MicroLogix 1200.

Current is supplied to each of the cells via rectifier 22. The D.C. rectifier will be preferably provided with a shunt trip circuit breaker, so that in the event the primary contactor remains closed after a loss of run signal, the shunt trip will be energized to drop all rectifier power. For example when operating at 240 volts ac, the rectifier is configured to transform the transform the voltage to 64 volts at 150 amps. Thus for a five cell system, each cell is separately wired at approximately 30 amps.

Because of fluctuations in flow rate, water temperature, etc. the actual, or effective current across each cell may also vary.

Unlike conventional electrochemical processes that rely on automatic, fixed-amperage control, the generation system 10 controls the electrolytic conversion process through process amperage control, which fixes the voltage applied to the cells and allows cell amperage to float within a narrow window. Rectifier 22 may thus simply comprise a fully isolated step-down transformer and bridge rectifier, foregoing the need for failure-prone SCR, phase angle, or wave form modification. Electrolytic cell density will generally be in the range of approximately 1.0-2.0 amps/square inch of active cell surface.

The process amperage control of system 10 is indirectly controlled by actively controlling the brine concentration in line 57 supplied to the flowing electrolyte. Thus, the voltage across cell 14 may be varied by increasing or decreasing the brine content at input 16, e.g. higher brine content will increase conductivity of the flowing electrolyte, and thus affect an increase in current. The active control is achieved using pump 49 that is incrementally adjustable to affect fine variation in the brine concentration. Pump 49 preferably comprises a magnetic drive, titanium gear pump which can be flow paced by the PLC 53.

Because the effective amperage may vary from cell to cell in the array, an additional line 75 may be fed into the one of the downstream cells to separately adjust electrolyte levels in that cell. For example, the first cell may have an effective current of 30 amps, the second cell may have an effective current of (30-n) amps, and the third cell may have an effective current of (30-2n) amps, and so on. With a separate input line 75 these variations may also be controlled.

This current feedback loop will therefore account for variations in water temperature, conductivity and flow rate without the need for problematic rectifier current control.

The control cabinet for the PLC 53 may also house and control variable frequency drives (VFD'S) dedicated to the hypochlorite metering pump 86 shown in FIG. 2. The VFD's may comprise NEMA 4 devices with integrated displays. The PLC 53 may be configured to accept analog inputs for both flow and residual flow for each VFD and drive an output signal to each VFD based on the appropriate flow, residual or compound algorithm. Each VFD will preferably be capable of being controlled manually regardless of the PLC status.

The system 10 may also have the following process safety interlocks, 1) analog water flow monitoring, 2) individual cell compartment level and flow switches, 3) dynamic cell pressure monitoring (DCP) system, 4) blower current sensing, 5) blower airflow via differential pressure and mechanical flow switch, and 6) sequential operations logic.

The DCP system actively monitors the cell electrolyte backpressure via the level sensor 69 and temperature switch 71, and determines if the pressure is within a normal window based on expected hydraulic and lift losses. The DCP system is preferably configured to instantly signal a closed output valve or open cell drain, precluding catastrophic cell failure or explosion even in the event of operator error of the electrolytic cell due to either ignition of the waste hydrogen gas or over pressurization of the cell body due to the evolution of hydrogen gas within a mistakenly valved-off cell vessel.

The DCP system constantly monitors internal cell pressure using an analog pressure sensor 69. The PLC logic 53 will constantly look at the pressure in terms of a normal window, e.g. 1.75-2.0 PSI. If the pressure is low, it would indicate an open drain valve or cell failure. If the pressure is high, it would indicate a closed outlet valve. Either abnormal scenario would cause an immediate shutdown, e.g. via temperature switch 71, within thirty (30) milliseconds of the event precluding catastrophic failure.

Sequential operations logic, or SOL, will also be employed in the system to look for shorted or bypassed safety sensors to preclude operation in the event of an SOL fault. For example, in the storage system 90 in FIG. 2, dilution blower 78 function may be controlled via sequential operations logic where upon each run cycle the following steps occur within the PLC logic in this specific order or a fault will occur: 1) system start, 2) blower call, 3) blower current draw achieved, 4) airflow switch made, 5) rectifier start.

The sodium hypochlorite generation system shown in FIG. 1 has a number of advantages over existing hypochlorite generation systems. First, the electrically active cell structure and bipolar electrodes in each cell 14 allow for high flow volume and minimize resistance heating. The design achieves rapid hydrogen separation to produce maximum gas lift at the electrode surface and minimize calcification of the electrodes. Not only is the efficiency of the system increased, but the components are much easier to manufacture. The system also naturally retains less calcacareous buildup, minimizing maintenance often required for existing systems. These elements of cell design directly affect overall system efficiency by minimizing electrolyte heat gain, calcium deposition and electrical consumption.

The vertical orientation and configuration of the electrolytic cells 14 allows for the instantaneous passive removal of all hydrogen produced. The re-circulating cell array 12 provides for many benefits: including reduced scaling potential, lower resistance, lower heat gain, lower chlorate formation and higher overall efficiencies.

Further, the system 10 has a number of safety features, including the ability to monitor flow in each cell compartment as opposed to the overall process. This ability to monitor compartmental flow, when combined with the passive hydrogen removal system, precludes the possibility of hydrogen entrapment and/or the potential of an explosion.

Redundant dynamic pressure transducers have also been included to sense a disruption in normal operating conditions, such as a broken pipe or mistakenly closed valve. Most, if not all, possible failure scenarios are taken into account, including direct operator error in the handling of the process equipment.

Sequential operations logic is also incorporated into the PLC 53 for all process variables, such that a change from standby to process is confirmed for all sensor locations at each start sequence. This auto diagnostic routine locks out generation in the event of sensor failure or electrical bypass.

While the system 10 and array 12 preferably use the electrolytic cell 14 of the present invention (having floating bipolar electrodes as shown in FIGS. 7-10), it is appreciated that the advantages of the system 10, (e.g. passive hydrogen removal, process amperage control, and the above-mentioned safety features, may be configured to use any electrolytic cell currently available in the art. Correspondingly, certain features of generation system 10, storage system 90, and delivery system 100 may be used interchangeably where desired or appropriate.

2. Treatment Solution Dosing and Delivery

Referring now to FIG. 3, a treatment delivery system 100 is shown that is configured to control and improve water chemistry and quality within large bodies of potable or reuse water such as municipal water reservoirs. Tank volumes typically range from 200,000 gallons to as large as 50 million gallons. System 100 is configured to have one or more of the following functions within a large body of water:

1. Mixing in order to achieve a homogenous solution.
2. Mixing to eliminate temperature stratification.
3. Sampling of mixed water and chlorine residual analysis.
4. Chemical injection directly within the flowing mixed water to allow for re-chlorination and improved water quality As depicted in FIG. 3, the system 100 is configured to maintain a body of water 108 inside reservoir 104 substantially free of temperature gradients and under high quality conditions suitable for end users.

A treatment solution is piped via dosing line 92 to the reservoir for treatment of the body of water 108. The treatment solution may comprise sodium hypochlorite, e.g. that generated from system 10 of FIG. 1, and stored in system 90 of FIG. 2. In addition, the system 100 may be used in any existing sodium hypochlorite generation system, or be used with other treatment solutions, such as ammonia, chlorine, chlorite gas, chlorite, chlorine dioxide, etc.

Figure 11:
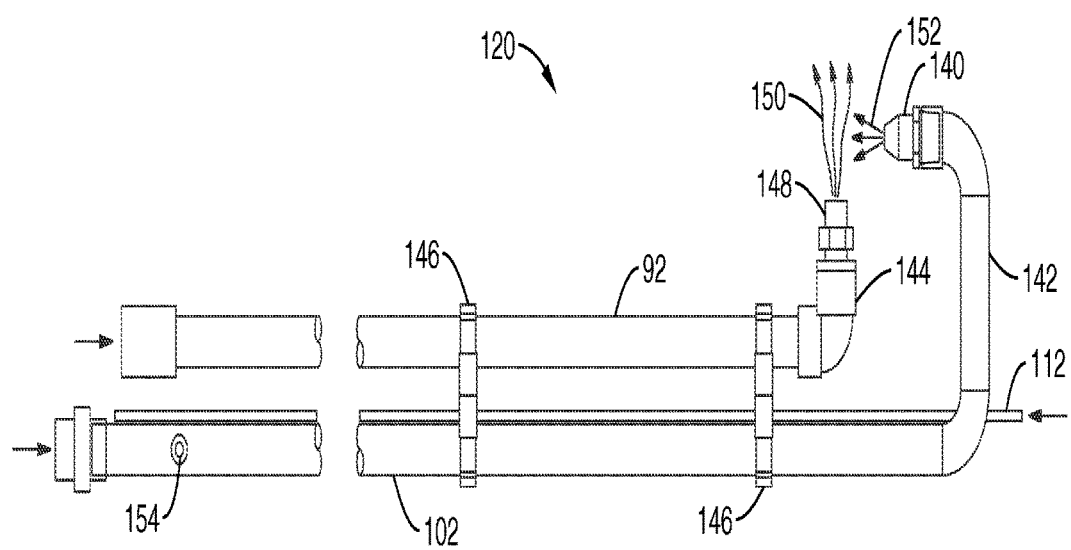
FIG. 11 shows an exemplary dosing assembly of the present invention.
Figure 12:
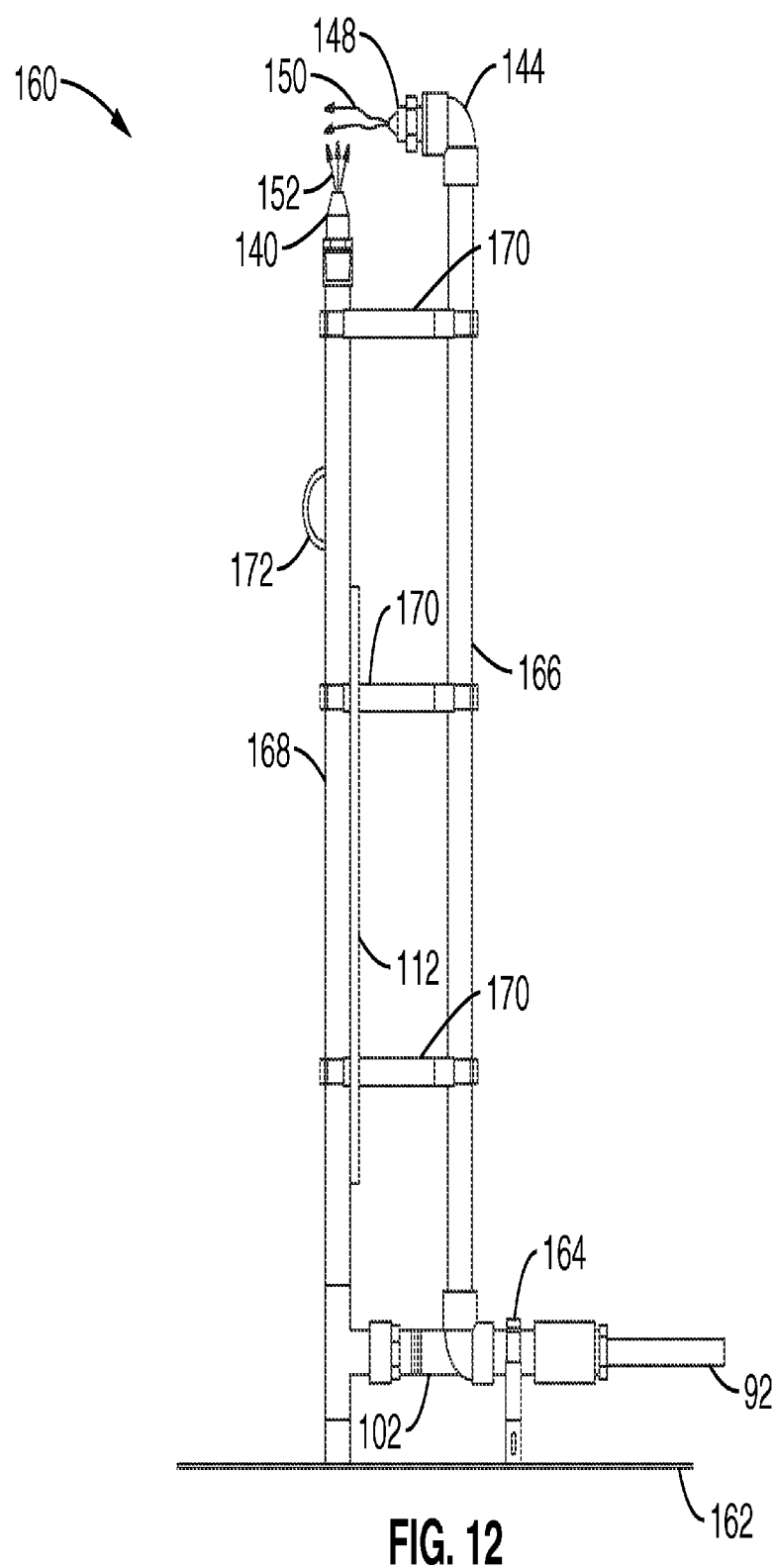
FIG. 12 shows a submersible dosing assembly in accordance with the present invention

In an embodiment utilizing the storage system 90 of FIGS. 3, 11, and 12, the treatment solution is pumped through inlet 114 and into reservoir 104 along dosing line 92 via a metering pump 86. In addition, water injection line 102 is fed into tanks 104 at inlet 114. The dosing line 92 and water injection line 102 extend vertically into the depths of tanks 104, and are generally held parallel to each other with a series of pipe clamps 146. A sample line 112 is also feed into tanks 104 at inlet 114 generally adjacent to injection line 102.

It is also appreciated that the treatment solution from storage tank 24 may be fed simultaneously into any number of reservoirs for treatment.

Referring now to FIGS. 11 and 12, the sample line 112, water injection line 102, and treatment line 92 emanate in the region of the dosing assembly 120. The treatment line 92 has a 90 degree elbow 144 that directs the treatment solution 150 (which preferably comprises sodium hypochlorite 88 generated from system 10) generally horizontally into the reservoir via valve 148. In addition, the water injection line 102 is oriented vertically upward via fitting 142, just below the release of treatment solution 150. Nozzle 140 directs a jet 152 of water upward into the treatment solution to disperse the treatment solution within the body of water 108 and also distributes the water 108 in the reservoir to disperse any temperature gradients in the water and prevent stagnation.

Nozzle 140 is generally a multiplying eductor with a high enough flow rate to generate an upward flow in the water. Exemplary nozzles include those available in the art, such as that shown and described in U.S. Pat. No. 5,894,995, incorporated herein by reference in its entirety. Nozzle 140 may infuse the jet 152 with both axial and rotational flow elements to disperse the body of water 108. The rotational aspect of the mixing nozzle 140 imparts angular momentum to the moving mass of tank water 108. Because the imparted angular momentum is conserved, the mass of water will begin to rotate if the stirring energy is added consistently in the same direction, similar to stirring a bowl of water with a toothpick.

The nozzle 140 may also be configured to expel water at different flow rates. However, the motive force for the jet 152 is generally the head pressure present in injection lines 102.

In one exemplary configuration, a 15 GPM multiplicative eductor nozzle 140 is placed within three to five feet of the base of the tank 108, causing an upward flow of water 152 equal to approximately five times the nozzle flow. This results in the addition of motive energy at the 15 GPM nozzle via approximately a 50 PSI pressure differential. This 15 GPM 150 PSI nozzle delivers an upward flow of approximately 75 GPM.

The configuration shown in FIGS. 3 and 11 functions to move colder water from the base of the reservoir up to and top of the warmer stratified layers. This thermal disruption causes additional mixing beyond the energy associated with the nozzle itself.

A pressure transducer 154 may also be included along line 102. In addition, the treatment solution 150 is generally expelled via control of an external pump, such as metering pump 86 of FIG. 2. Thus, no internal pump is necessary inside the reservoir to disperse the treatment solution and body of water. This greatly increases reliability and serviceability of the systems over existing systems with internal pumps.

FIGS. 3 and 11 illustrate the dosing assembly 120 suspended from the top of tank 108. However, FIG. 12 illustrates an alternative dosing assembly 160 that is configured to be directly submersed within a frame 162 that rests at the bottom of the tank 104. The submersed dosing assembly 160 is configured to be remotely positioned via cable guide 172 and stainless steel guide cables on to pre-positioned anchors (not shown) at the bottom of the tank.

The submersible dosing assembly has a motive tube 168 that is coupled to water injection line 102 at a first end and secured to the frame 162. The other end of tube 168 comprises eductor nozzle 140 that directs motive jet 152 upward into the body of water 108. Treatment line 92 is couple to a treatment flow tube 166 that is also secured to the frame 162 via bracket 164. The tubes 168 and 166 are spaced generally parallel to each other via a series of braces 170. Elbow 144 directs the flow of tube 166 such that injection quill 148 directs treatment solution 150 into jet 152 for diffusion into the tank. It is appreciated that a plurality of treatment quills 148 may be directed at jet 152, e.g. in a radial array pointing inward toward jet 152. Each quill may have an independent treatment line supplying a treatment solution. For example, a first quill 148 may inject sodium hypochlorite, while a second quill (not shown) injects a stream of ammonia.

In another aspect of the invention, the chemistry of the body of water 108 may be maintained by continuous sampling of the water and adjustment of the dosing rate of the chemicals added to the water. Accordingly, a small jet of water is extracted on a continuous basis along sample line 112 via rotary gear pump 122 (or pump and recovery tank 126 for reservoir 106) to the analyzer 124 to measure the free chlorine and total chlorine in the body of water. A typical pump 122 is capable of drawing 0.25-0.75 GPM of representative water and driving that sample to the chlorine residual analyzer 124 to determine the water quality on a continuous basis. The extracted water may be disposed, or held in recovery tank 126 for insertion back into the reservoir 104.

The analyzer may be coupled to a controller, such as PLC 53 shown in FIG. 1, which compares the chlorine or chloramine-related measurement signals with a set point, and then determines whether the amount of chlorine in the water should be maintained, or adjusted upwardly or downwardly. If adjustment is needed, a signal from the controller may be sent to metering pumps 86 to increase or decrease the flow of treatment solution (e.g. sodium hypochlorite) into the reservoir. Typically, free chlorine and chloramines levels are maintained in the range of 0.01 to 10 ppm in the reservoir.

It is appreciated that although treatment system 100 is preferably used in conjunction with hypochlorite generation system 10 and storage system 90 of the present invention, the features of system 100 may be configured to accommodate any source of treatment solution commonly available in the art. For example, the dosing assembly 120 may be used to deliver ammonia in conjunction with, or in place of, a second dosing assembly for delivering sodium hypochlorite, similar to that disclosed in U.S. Pat. No. 6,811,710, herein incorporated by reference in its entirety. If the residual analysis determines deficiency in chlorine or ammonia, either or both chemicals are then injected into the 75 GPM upward flowing stream of water 152 for dilution and mixing within the tank volume.

The system 100 of the present invention is shown with one dosing assembly 120 per tank. However, one or more nozzles may similarly be placed at varying locations within the tank.

The system 100 is also capable of injecting multiple chemicals within the same stream of flowing water. For example, the injection of hypochlorite and ammonia to produce chloramines within the flowing stream.

3. Oxygen Generation for Contaminant Removal

Figure 13:
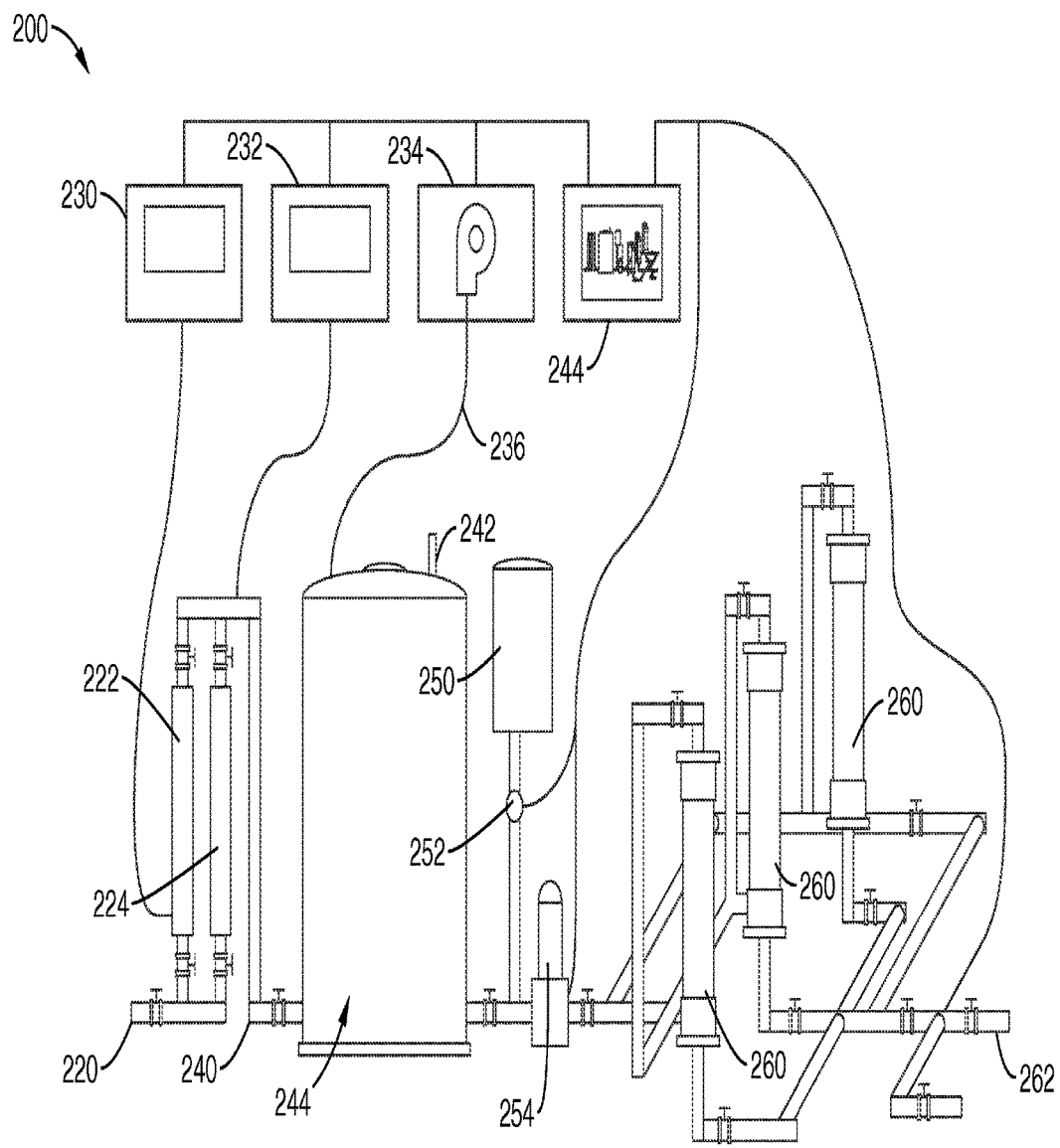
FIG. 13 shows an oxygen generation system in accordance with the present invention.

Referring now to FIG. 13, a method and system 200 utilizing oxygen ($O_2$) generation for contaminant removal is illustrated. System 200 combines three unique treatment operations to remove contaminants without the need for hazardous chemicals or filter medias. First, untreated water is oxidized. Next the oxygen infused water is subject to iron ionization to flocculate the undesirable components in the water. Finally, the water is filtered to remove the floccules.

Oxidation is accomplished by the electrolytic generation of nascent oxygen utilizing the raw water itself. As shown in FIG. 8, untreated water is fed into the system 200 at inlet 220. The water is first drawn through electrolytic cell 222. Electrolytic cell uses electrical current supplied by rectifier 230 to liberate hydrogen from the water, thus oxidizing the water with $O_2$ under the following process:

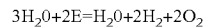

$$3H_2O+2E=H_2O+2H_2+2O_2$$

The electrolytic cell 222 may be identical to the electrolytic cell 14 shown in FIGS. 7-10, which the exception that the electrode endplates 40/42, and electrode 44 are coated with platinum rather than DSA.

The oxidation step allows for the removal of any entrained or dissolved gasses, destruction of any nitrogen compounds, nitrate, ammonia, etc., removal of any volatile organic compounds and oxidation of any inorganic compounds such as iron.

The oxygen produced by the oxygen generation system 200 has many beneficial effects. When combined with the iron ions produced by the electro-phoretic iron cell 224 (explained in further detail below), it can speed up chemical reactions, oxidize unwanted materials, kill bacteria, lower the surface tension of the water to allow for more efficient flocculation and precipitation and supply needed oxygen demand.

Figure 14:
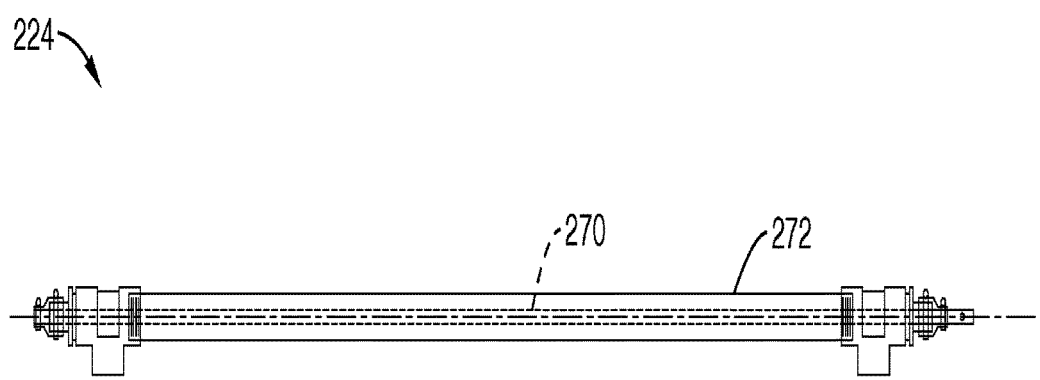
FIG. 14 illustrates an iron-pass cell in accordance with the present invention.

The oxidized water is then passed through an electrophoretic iron cell 224, which is shown in greater detail in FIG. 14. Preferable, iron cell 224 comprises a two-pass cell, having a solid inner iron rod concentrically positioned inside an outer iron pipe. A second rectifier 232 is coupled to the cell to pass a current through the cell to generate iron ions that are infused into the passing water.

The iron ions produced by the electro-phoretic cell 224 react with oxygen to form other species or iron, which in turn, attract other elements to form safer compounds or to flocculate (i.e. coagulate) into larger particles for more efficient removal by filtration or precipitation. Many harmful materials are converted to iron compounds that are removed by the filter and become non-leachable, allowing for non-hazardous disposal.

The flocculated water is then feed via line 240 into reactor tank 244. Diffusion blower 234 is fed into the upper portion of reactor tank 244 via inlet 236. The blower serves to remove the hydrogen generated from the electrolytic process out through vent 242. A precoat stored in precoat holding tank 250 is then applied via jet pump 252 to the water exiting from the reactor tank at line 254. Centrifugal pump 254 then drives the water through into one or more filters 260.

All operations, including the control of the rectifiers 230/232, dilution blower 234, and pumps 252, 254, are controlled with PLC 244.

Solids removal is performed using filter media such as diatomaceous earth. Filters 260 allow for filtration of solids down to 0.1 micron. Filters 260 preferably use a unique septum to collect the filter media. The septum creates a deeper filter bed while using less media per gpm than conventional pre-coat filters. This design allows for more efficient backwashing and pre-coating.

Filters 260 are preferably in parallel to permit continuous operation during backwash and pre-coat modes. The backwash water is routed through a bag filter system to remove the spent media while returning the water to the front of the treatment system with no loss of product volume. The spent media dewaters easily and the relatively small volume of media versus water flow makes disposal a simple process.

The system 200 is configured to thoroughly remove contaminants from ground water, surface water and municipal and industrial wastewaters. The three step process for extracting contaminants produces water quality that surpasses the most stringent standards.

The flexible modular design of system 200 allows for implementation with a minimum footprint and higher reliability than conventional treatment systems. The unique features of system 200 also allow for a lower overall operating cost, no hazardous chemicals, simple operation and process control combined with lower capital cost and easy installation for a very competitive package. There is no wasted product water, such as in the brine disposal required by membrane or ion exchange systems. All water treated is product water. There are no cartridges or filter elements to replace or dispose of, only dried, inexpensive filter media. No hazardous waste is generated. Pre-treatment with the system 200 process can actually lessen the operating cost of processes downstream.

The system 200 can be used as a pretreatment to improve the quality of an existing process, as a stand alone system, or as a post-treatment process to improve final water quality, with higher reliability and lower overall operating cost than most conventional treatment systems. Capital and operating costs are determined by site specific pilot testing where each contaminant of concern is specifically addressed.

The system 200 may be used as a pretreatment process, before conventional applications such as lime softening and membranes.

The system 200 is a modular system of components that are tailored to the specific application. Depending on the application, the system can be built onsite or provided as a skid. Because the system is modular, it is simple to plan for future expansion and growth as required.

The system 200 has the following removal capabilities: iron & manganese, arsenic, TOC/DBP precursors, ammonia, organic & inorganic materials, hydrocarbons, heavy & semi-heavy metals, color, and H2S Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

The invention claimed is:

1. A treatment delivery system for treatment of a body of water held in a reservoir, the treatment delivery system comprising:
   a chemical dosing assembly submersible within the body of water comprising a frame adapted to rest at the bottom of the reservoir, a water motive tube secured to the frame, and a first chemical treatment flow tube secured to the frame;
   wherein each of the water motive tube and the first chemical treatment tube independently comprises a first end having an inlet attached to a top surface of the frame and a second end oriented above the first end within the reservoir and having an outlet;
   wherein the second ends of the water motive and chemical treatment flow tubes extend vertically from the top surface of the frame and in which the water motive and chemical treatment flow tubes are generally held parallel to each other; and
   wherein the outlet of the water motive tube is oriented to expel a jet of water generally upward into the body of water held in the reservoir, and the outlet of the first chemical treatment flow tube is oriented to inject treatment solution into the jet of water expelled by the outlet of the water motive tube.

2. The system of claim 1, further comprising a second chemical treatment flow tube secured to the frame,
   wherein the second chemical treatment flow tube independently comprises a first end having an inlet attached to a top surface of the frame and a second end oriented above the first end within the reservoir and having an outlet,
   wherein the second end of the second chemical treatment flow tube extends vertically from the top surface of the frame and in which the second chemical treatment flow tube is generally held parallel to the water motive tube and the first chemical treatment flow tube, and wherein the outlet of the second chemical treatment flow tube is oriented to inject treatment solution into the jet of water expelled by the outlet of the water motive tube.

3. The system of claim 2, wherein the first chemical treatment flow tube is configured to inject hypochlorite and the second chemical treatment flow tube is configured to inject ammonia.

4. The system of claim 1, wherein the treatment solution is injected generally horizontally across the jet of water.

5. The system of claim 1, wherein the outlet of the water motive tube is positioned below the outlet of the first chemical treatment flow tube.

6. The system of claim 5, wherein the second end of the first chemical treatment flow tube comprises a 90 degree elbow that directs the treatment solution generally horizontally across the jet of water.

7. The system of claim 1, wherein the outlet of the water motive tube comprises an eductor nozzle.

8. The system of claim 1, wherein the outlet of the first chemical treatment flow tube comprises an injector quill.

9. The system of claim 1, further comprising a water sampling line for receiving a sample from the body of water.

10. The system of claim 9, wherein the water sampling line is positioned below the outlets of both the water motive tube and the first chemical treatment flow tube.

11. The system of claim 9, further comprising an analyzer in fluid communication with the water sampling line, wherein the analyzer is configured to measure at least one chemical found in a sample of water collected by the water sampling line.

12. The system of claim 11, further comprising a controller coupled to the analyzer, wherein the controller is configured to compare a measurement of a chemical obtained by the analyzer with a set point of the chemical and determine whether the amount of the chemical in the body of water should be maintained or adjusted.

13. The system of claim 1, further comprising a cable guide attached to the water motive tube.

14. A method of treating a body of water held in a reservoir, the method comprising:
(a) supplying a treatment solution to a chemical dosing assembly submerged within the body of water, the chemical dosing assembly comprising:
(i) a frame that rests at the bottom of the reservoir,
(ii) a water motive tube secured to the frame, and
(iii) a first chemical treatment flow tube secured to the frame, wherein each of the water motive tube and the first chemical treatment flow tube independently comprises a first end having an inlet attached to a top surface of the frame and a second end oriented above the first end in the reservoir and having an outlet;
(b) delivering, from the outlet of the water motive tube, a jet of water upwards into the body of water held in the reservoir; and
(c) delivering, from the outlet of the first chemical treatment flow tube, the treatment solution into the jet of water,
wherein the second ends of the water motive and chemical treatment flow tubes extend vertically from the top surface of the frame and in which the water motive and chemical treatment flow tubes are generally held parallel to each other.

15. The method of claim 14, wherein the chemical dosing assembly further comprises a second chemical treatment flow tube secured to the frame, the second chemical treatment flow tube independently comprising a first end having an inlet attached to the top surface of the frame and a second end oriented above the first end within the reservoir and having an outlet,
wherein the second end of the second chemical treatment flow tube extends vertically from the top surface and in which the second chemical treatment flow tube is generally held parallel to the water motive tube and the first chemical treatment flow tube.

16. The method of claim 15, further comprising:
delivering, from the outlet of the second chemical treatment flow tube, a treatment solution into the jet of water, wherein the treatment solution delivered by the second chemical treatment flow tube is different than the treatment solution delivered by the first chemical treatment flow tube.

17. The method of claim 16, wherein the treatment solution delivered by the first chemical treatment flow tube comprises hypochlorite and the treatment solution delivered by the second chemical treatment flow tube comprises ammonia.

18. The method of claim 14, further comprising extracting a sample of water with a water sampling line secured to the chemical dosing assembly, and analyzing the sample of water.

19. The method of claim 18, further comprising comparing a measured amount of a chemical in the water sample to a set point of the desired amount of the chemical in the water sample and determining, based on the comparison, whether the amount of the chemical in the body of water should be maintained or adjusted.

20. The method of claim 19, wherein a flow rate of the treatment solution is adjusted to obtain a desired amount of the chemical in the body of water.

21. The method of claim 20, wherein the chemical is at least one of chlorine and chloramine.

* * * * *